(12) United States Patent
Kay et al.

(10) Patent No.: US 6,767,899 B1
(45) Date of Patent: Jul. 27, 2004

(54) COMPOSITION AND METHOD FOR TREATMENT OF CONDITIONS HAVING AN INFLAMMATORY COMPONENT

(75) Inventors: Robert A. Kay, LaMirada, CA (US); Larry K. Thomas, Irvine, CA (US); Beuford A. Bogue, Carson, CA (US)

(73) Assignee: Leiner Health Services Corp., Carson, CA (US)

( * ) Notice: Subject to any disclaimer, the term of this patent is extended or adjusted under 35 U.S.C. 154(b) by 219 days.

(21) Appl. No.: 09/650,055

(22) Filed: Aug. 29, 2000

(51) Int. Cl.[7] .......................... A61K 31/70; C07H 5/04; C07H 5/06
(52) U.S. Cl. ...................... 514/62; 424/461; 536/55.2
(58) Field of Search .................... 514/62; 536/55.2; 424/461

(56) References Cited

U.S. PATENT DOCUMENTS

| | | | |
|---|---|---|---|
| 3,683,076 A | 8/1972 | Rovati | 424/180 |
| 3,911,098 A | 10/1975 | Capozza | 424/22 |
| 4,006,224 A | 2/1977 | Prudden | 424/180 |
| 4,228,161 A | 10/1980 | Shen | 424/232 |
| 4,647,453 A | 3/1987 | Meisner | 424/54 |
| 4,704,268 A | 11/1987 | Kifune | 424/488 |
| 4,772,591 A | 9/1988 | Meisner | 514/62 |
| 5,364,845 A | 11/1994 | Henderson | 514/54 |
| 5,582,837 A | 12/1996 | Shell | 424/431 |
| 5,587,363 A | 12/1996 | Henderson | 514/54 |
| 5,681,585 A | 10/1997 | Oshlack et al. | 424/474 |
| 5,716,631 A | 2/1998 | Drizen et al. | 424/422 |
| 5,736,152 A | 4/1998 | Dunn | 424/426 |
| 5,840,715 A | 11/1998 | Florio | 514/62 |
| 5,843,919 A | 12/1998 | Burger | 514/62 |
| 5,846,952 A | 12/1998 | Vournakis et al. | 514/55 |
| 5,849,336 A | 12/1998 | Aoyagi et al. | 424/570 |
| 5,855,915 A | 1/1999 | Pinkus | 424/407 |
| 5,888,514 A | 3/1999 | Weisman | 424/195.1 |
| 5,916,565 A | 6/1999 | Rose et al. | 424/195.1 |
| 5,994,324 A | 11/1999 | Ashida et al. | 514/57 |
| 6,007,843 A | 12/1999 | Drizen et al. | 424/488 |
| 6,020,002 A | 2/2000 | Myers et al. | 424/488 |
| 6,046,179 A | 4/2000 | Murch et al. | 514/17 |

OTHER PUBLICATIONS

Baron et al., "Glucosamine Induces Insulin Resistance In Vivo By Affecting GLUT 4 Translocation in Skeletal Muscle," *J. Clin. Investigation, Inc.*, 96:2792–2801, (Dec. 1995).

McClain et al., "Hexosamines and Insulin Resistance," *Diabetes*, #45:1003–1009, (1996).

Rege et al., "Chitosans as Tableting Excipients for Modified Release Delivery Systems (Abstract)," *Int. J. Pharm*, 181 (1):49–60, (Apr. 20, 1999).

*Primary Examiner*—Dwayne C. Jones
(74) *Attorney, Agent, or Firm*—Hoffmann & Baron, LLP

(57) ABSTRACT

Compositions and methods of treatment for conditions in humans and animals which have an inflammatory component, are disclosed. The composition comprises a glucosamine component dispersed in a controlled-release matrix system capable of releasing the glucosamine over a designated time period. In another aspect, the invention provides compositions and methods for the treatment of arthritis in humans and animals without adversely effecting glucose regulation.

46 Claims, 5 Drawing Sheets

COMPOSITION AND METHOD FOR TREATMENT OF CONDITIONS HAVING AN INFLAMMATORY COMPONENT

BACKGROUND OF THE INVENTION

The present invention relates to therapeutic compositions and methods of treatment for conditions having an inflammatory component, and more specifically bone, joint or connective tissue inflammation. Examples of such conditions include arthritis, including osteoarthritis and rheumatoid arthritis, rheumatism, tendonitis, bursitis, degenerative spinal disc disease, and trauma to joints, tendons, and ligaments, including sports trauma.

Inflammation, as defined in Dorland's Medical Dictionary, is "a localized protective response elicited by injury or destruction of tissues which serves to destroy, dilute or wall off both the injurious agent and the injured tissue." It is characterized by dilation of the microvasculature, leakages of the elements of blood into the interstitial spaces, and migration of leukocytes into the inflamed tissue. On a macroscopic level, this is usually accompanied by the familiar clinical signs of erythema (redness), edema (fluid buildup), hyperalgesia (tenderness), heat, and pain. During this complex response, chemical mediators such as histamine, 5-hydroxytryptamine, various chemotactic factors, bradykinin, leukotrienes, and prostaglandins are liberated locally. Phagocytic cells migrate into the area, and cellular lysosomal membranes may be ruptured, releasing lytic enzymes. All of these events may contribute to the inflammatory response.

Inflammation in patients with rheumatoid arthritis probably involves the combination of an antigen (gamma globulin) with an antibody (rheumatoid factor) and complement causing the local release of chemotactic factors that attract leukocytes. The leukocytes phagocytose the complexes of antigen-antibody and complement and also release the many enzymes contained in their lysosomes. These lysosomal enzymes then cause injury to cartilage and other tissues, and this furthers the degree of inflammation. Cell mediated immune reactions may also be involved. Prostaglandins are also released during this process.

Prostaglandins, which are likely to be generated in inflammation, cause erythema and increase local blood flow. Two important vascular effects of prostaglandins that are not generally shared by other mediators of inflammation are a long-lasting vasodilator action and a capacity to counteract the vasoconstrictor effects of substances such as norepinephrine and angiotensin.

A number of mediators of inflammation increase vascular permeability (leakage) in the post-capillary and collecting venules. In addition, migration of leukocytes into an inflamed area is an important aspect of the inflammatory process.

Although osteoarthritis does not always include the same intense inflammatory component as rheumatoid arthritis, it does involve damage to cartilage and other tissues, resulting in pain, deformity, and limitation of motion of joints, in a similar fashion to rheumatoid arthritis.

Osteoarthritis is divided into two categories, primary and secondary osteoarthritis. In primary osteoarthritis, the degenerative wear-and-tear process generally occurs after the fifth and sixth decades, with no predisposing abnormality apparent. The cumulative effects of decades of use leads to the degenerative changes by stressing the integrity of the collagen matrix of the cartilage. Damage to the cartilage results in the release of enzymes that destroy collagen components. With aging, there is a decreased ability to restore and synthesize normal collagen structures.

Secondary osteoarthritis is associated with some predisposing factor responsible for the degenerative changes. Various predisposing factors in secondary osteoarthritis include congenital abnormalities in joint structure or function (e.g. excessive joint mobility and abnormally shaped joint surfaces), trauma (obesity, fractures along joint surfaces, surgery, etc.), crystal deposition, presence of abnormal cartilage, and previous inflammatory disease of joint (rheumatoid arthritis, gout, septic arthritis, etc.)

The causes of osteoarthritis are, thus, believed to include one or more of the following conditions or imbalances in the body's chemistry: excessive mobility/joint instability, age-related changes in collagen matrix repair mechanisms, hormonal and sex factors, altered biochemistry, genetic predisposition, inflammation, fractures and mechanical damage, inflammatory joint disease, joint immobilization, poor nutritional history, and others.

As anyone who has been afflicted by this disease can attest, the onset of osteoarthritis can be very subtle, morning joint stiffness often being the first symptom. As the disease progresses, there is pain on motion of the involved joint, that is made worse by prolonged activity and relieved by rest. There is usually only minor inflammation.

The specific clinical picture varies with the joint involved. Disease of the hands leads to pain and limitation of use. Knee involvement produces pain, swelling, and instability. Osteoarthritis of the hip causes local pain and a limp. Spinal osteoarthritis is very common and may result in compression of nerves and blood vessels, causing pain and vascular insufficiency.

The inflammatory response is any response characterized by inflammation as defined above. It is well known to those skilled in the medical arts that the inflammatory response causes much of the physical discomfort, i.e., pain and loss of function, that has come to be associated with different diseases and injuries. Accordingly, it is a common medical practice to administer pharmacological agents which have the effect of neutralizing the inflammatory response. Agents having these properties are classified as anti-inflammatory drugs. Anti-inflammatory drugs are used for the treatment of a wide spectrum of disorders, and the same drugs are often used to treat different diseases. Treatment with anti-inflammatory drugs is not for the disease, but most often for the symptom, i.e., inflammation.

The anti-inflammatory, analgesic, and anti-pyretic drugs are a heterogeneous group of compounds, often chemically unrelated, which nevertheless share certain therapeutic actions and side-effects. Corticosteroids represent the most widely used class of compounds for the treatment of the inflammatory response. Proteolytic enzymes represent another class of compounds which are thought to have anti-inflammatory effects. Hormones which directly or indirectly cause the adrenal cortex to produce and secrete steroids represent another class of anti-inflammatory compounds. A number of nonhormonal anti-inflammatory agents have been described. These agents are generally referred to as non-steroidal anti-inflammatory drugs (NSAIDS). Among these, the most widely used are the salicylates. Acetylsalicylic acid, or aspirin, is the most widely prescribed analgesic-antipyretic and anti-inflammatory agent. Examples of steroidal and non-steroidal anti-inflammatory agents are listed in the *Physicians Desk Reference*, 54Edition, 2000 (see pp. 202 and 217 for an index of such preparations).

The natural and synthetic corticosteroid preparations cause a nunber of severe side effects, including elevation of blood pressure, salt and water retention, and increased potassium and calcium excretion. Moreover, corticosteroids may mask the signs of infection and enhance dissemination of infectious microorganisms. These hormones are not considered safe for use in pregnant females, and long-term corticosteroid treatment has been associated with gastric hyperactivity and/or peptic ulcers. Treatment with these compounds may also aggravate diabetes mellitus, requiring higher doses of insulin, and may produce psychotic disorders. Hormonal anti-inflammatory agents which indirectly increase the production of endogenous corticosteroids have the same potential for adverse side-effects.

NSAIDS are synthetic biochemical compounds which can be toxic at high doses with a wide spectrum of undesirable side-effects. For example, salicylates contribute to the serious acid-base balance disturbances that characterize poisoning by this class of compounds. Salicylates stimulate respiration directly and indirectly. Toxic doses of salicylates cause central respiratory paralysis as well as circulatory collapse secondary to vasomotor depression. The ingestion of salicylate may result in epigastric distress, nausea, and vomiting. Salicylate-induced gastric bleeding is well known. Salicylates can produce hepatic injury, and lead to a prolongation of clotting time. Therefore, aspirin should be avoided with patients with severe hepatic damage, hypoprothrombinemia, vitamin K deficiency, or hemophilia, because the inhibition of platelet homeostasis by salicylates can result in hemorrhage. Salicylate intoxication is common, and over 10,000 cases of serious salicylate intoxication are seen in the United States every year, some of them being fatal, and many occurring in children. See Goodman and Gilman's The Pharmacological Basis of Therapeutics, 9 Ed., 1992.

Another side effect of aspirin and other NSAIDs that is often not mentioned is their inhibition of cartilage repair (i.e. inhibition of collagen matrix synthesis) and acceleration of cartilage destruction in experimental studies. Since osteoarthritis is caused by a degeneration of cartilage, it appears that, while NSAIDs are fairly effective in suppressing the symptoms, they possibly worsen the condition by inhibiting cartilage formation and accelerating cartilage destruction. This adverse effect of NSAID therapy has been upheld in studies which have shown that NSAIDs use is associated with acceleration of osteoarthritis and increased joint destruction. Simply stated, NSAIDs appear to suppress the symptoms but accelerate the progression of osteoarthritis. Accordingly, in spite of the large number of anti-inflammatory agents that are currently available, there still exists a need for a safe, effective anti-inflammatory product which is free of side-effects and adverse reactions.

Natural ingredients, including Ayurvedic formulations, have been used to treat bone and joint inflammation, especially in eastern countries, and, increasingly, in western countries. Such natural ingredients include, for example, cartilage, chondroitin, glucosamine, proteolytic and other enzymes, and herbs, such as the gummy extract of *B. serrata*, Ashwagandha root and ginseng root. Although such natural ingredients generally do not lead to the kind of side effects observed with the steroidal and non-steroidal anti-inflammatory drugs (NSAIDS) discussed above, many of these natural ingredients do not always provide sufficient relief of pain or restoration of significant function and use of inflammed tissue, e.g., joints. However, glucosamine and chondroitin have been found to contribute to restoring such function and use.

Although glucosamine generally does not provide the same rapid temporary relief of inflammation and pain as aspirin or other non-steroidal anti-inflammatory drugs (NSAIDS), it plays several key roles in the preservation and rebuilding ofjoint tissues. Namely, it stimulates the cartilage cells to produce glycosaminoglycans and proteoglycans, which maintain healthy joints and contribute to rebuilding connective tissue, and it is one of the main ingredients of the synovial fluid that lubricates and provides nutrients for the joint structures. By participating in the preservation and rebuilding ofjoint tissues, it is believed that glucosamine can contribute to long term relief of a wide range of degenerative and inflammatory conditions such as rheumatoid arthritis, osteoarthritis, degenerative spinal disc disease, tendinitis, bursitis, and trauma to joints, tendons and ligaments, and may actually reverse the underlying disease process, in many cases.

Chondroitins, e.g. chondroitin sulfate, have also been found to play a role in the preservation and rebuilding ofjoint tissues. In a similar fashion to glucosamine, chondroitins have been found to stimulate cartilage cells to produce the needed proteoglycans and to inhibit the enzymes that break down proteoglycans. Chondroitin sulfate in particular also functions to draw fluid into the proteoglycan molecules. This fluid acts as a shock absorber for the joint tissue and also carries nutrients into the cartilage.

Although the administration of glucosamine appears to be an effective treatment for many conditions having an inflammatory component, it is not free of side effects. In that regard, it has been found that high blood serum levels of glucosamine can interfere with glucose regulation in both normal individuals and individuals with diabetes mellitus. The high levels of glucosamine can induce an insulin resistance response, resulting in reduced rates of insulin-mediated glucose uptake by the liver, skeletal muscle, and adipose tissue (fat cells). If uncontrolled, insulin resistance can lead to hyperglycemia and possibly glucose toxicity. In normal (i.e., non-diabetic) individuals, hyperglycemia can interfere with cellular metabolism and the mechanics for insulin-induced glucose disposal. The hyperglycemia itself can worsen insulin resistance, thus contributing to a vicious cycle that makes glycemic regulation more difficult. Moreover, hyperglycemia and insulin resistance are major contributing factor in the pathogenesis of non-insulin-dependant diabetes mellitus (NIDDM).

The effects of high glucosamine levels on patients with NIDDM are typically more pronounced, since such patients generally affect glycemic regulation with dietary control. Thus, in such patients the cause and effect of insulin resistance and hyperglycemia on each other result in worsening the diabetic state and making glycemic regulation more difficult. Moreover, clinical studies have shown that hyperglycemia is the cause of most if not all of the chronic complications of diabetes. Insulin resistance induced by high levels of glucosamine can also have dramatic effects on patients with insulin dependent diabetes mellitus (IDDM) by again initiating a vicious cycle that worsens the diabetic state and makes glycemic regulation more difficult, possibly leading to glucose toxicity.

Thus, there is a need for new treatments of conditions having an inflammatory component, such as inflammed bones and/or joints, that avoid the disadvantages of known treatments, including the disadvantages described above.

SUMMARY OF THE INVENTION

The present invention is a composition and method for the treatment of a condition having an inflammatory component.

Treatment of such conditions in accordance with the present invention contributes to both long term relief of the symptoms associated with the inflammatory condition and restoration of finction and use of inflammed tissue (e.g., bones and joints), without the side effects attributable to more conventional steroidal anti-inflammatory drugs and NSAIDS, such as aspirin.

In one aspect, the invention relates to a controlled-release glucosamine composition which contains a therapeutically effective amount of a glucosamine component dispersed in a controlled-release matrix system capable of releasing the glucosamine in an amount and at a rate sufficient to maintain an effective glucosamine blood serum level over a designated time period. The controlled-release matrix system contains a controlled-release component which contains at least one water soluble cellulose polymer, preferably at least one water soluble high molecular weight cellulose polymer.

Preferably, the glucosamine component is selected from the group consisting of N-acetyl-D-glucosamine, glucosamine hydrochloride, glucosamine sulfate and mixtures thereof A typical dosage according to the invention ranges from about 2 mg to about 45 mg of glucosamine per kilogram of body weight per 24 hour period. Preferably, the daily dosage is from about 14 mg to about 29 mg and more preferably about 21 mg per kilogram of body weight.

The controlled-release component is preferably selected from the group consisting of hydroxypropyl methyl cellulose (HPMC), hydroxyethyl cellulose (HEC), hydroxy propyl cellulose (HPC), carboxy methyl cellulose (CMC), and mixtures thereof. The most preferred controlled-release component is HPMC.

The HPMC is preferably a high molecular weight HPMC, having an average molecular weight of at least about 25,000, more preferably at least about 65,000 and most preferably at least about 85,000.

The HPMC preferably consists of fine particulates having a particle size such that not less than 80% of the HPMC particles pass through an 80 mesh screen.

The HPMC can be included in an amount of from about 4 to about 24 wt %, preferably from about 6 to about 16 wt % and more preferably from about 8 to about 12 wt %, based upon total weight of the composition.

In a preferred embodiment, the controlled-release matrix system is capable of releasing the glucosamine at a substantially constant rate over the designated time period. Preferably, the controlled-release matrix system is capable of releasing the glucosamine at a substantially constant rate over a designated time period selected from about 6, 8, 12 and 24 hours. More preferably the designated time period is about 12 hours.

The composition is preferably in a form suitable for oral administration. This form can be a tablet and more preferably a tablet capable of releasing glucosamine at a substantially constant rate over a designated time period of about 12 hours. Such a tablet can contain HPMC, having an average molecular weight of about 85,000, as the controlled-release component in an amount of, for example, about 10 wt %.

In addition to the glucosamine component, the composition can optionally include a therapeutically effective amount of chondroitin sulfate. The daily dosage of chondroitin sulfate ranges from about 100 mg to about 2400 mg. Preferably, the daily dosage is from about 200 mg to about 1800 mg and more preferably about 1200 mg, based upon a 70 kg human or animal.

The invention also provides a unit dosage for controlled delivery of glucosamine which contains a therapeutically effect amount of a glucosamine component dispersed in a controlled-release matrix system containing a controlled-release component capable of providing a release profile which results in a substantially constant release of glucosamine over a designated time period.

The unit dosage is preferably in a form suitable for oral administration. More preferably, the unit dosage is a tablet. The tablet preferably contains about 8 to about 12 wt % HPMC, having a molecular weight of about 85,000, and is designed to release the glucosamine over about a 12 hour period.

In another aspect, the invention is a method for the treatment of conditions having an inflammatory component which involves: administering to a human or animal having a condition with an inflammatory component a composition which contains a therapeutically effective amount of a glucosamine component dispersed in a controlled-release matrix system capable of releasing the glucosamine in an amount and at a rate sufficient to maintain an effective glucosamine blood serum level over a designated time period, the controlled-release matrix system containing a controlled-release component which contains at least one water soluble cellulose polymer.

The composition being administered is preferably the controlled-release glucosamine composition, as described above, and more preferably the unit dosage, as described above.

In an especially preferred embodiment, the method also involves maintaining an effective glucosamine blood serum level, by continually repeating the administering step at the expiration of the designated time period, so as to relieve the inflammatory component of the condition. For example, where the designated time period is 12 hours, the method can be carried out by a continued regimen of administering one dosage every 12 hours to maintain a substantially constant release of glucosamine over a time sufficient to provide relief from the inflammatory condition.

In another aspect, the invention is directed towards a composition for the treatment of arthritis without adversely effecting glucose regulation, the composition containing a therapeutically effective amount of a glucosamine component dispersed in a controlled-release matrix system capable of releasing the glucosamine in an amount and at a rate sufficient to maintain an effective glucosamine blood serum level for treatment of arthritis, but not to exceed a glucosamine blood serum level which will affect an adverse change in glucose regulation, over a designated time period.

The adverse change in glucose regulation refers to increased difficulty in metabolizing blood serum glucose and can be manifested by increased insulin resistance. In such a case, the composition will release glucosamine in an amount and at a rate which provides a glucosamine blood serum level that does not exceed the level which will induce an insulin resistance response.

The composition according to this aspect of the invention can be used for the treatment of arthritis in humans and animals having both arthritis and a condition in which the ability to metabolize carbohydrates is reduced, such as, for example, diabetes or syndrome X, without adversely effecting glucose regulation, e.g., without inducing an insulin resistance response.

The composition in accordance with this aspect of the invention can include the controlled-release glucosamine composition, as described above, provided that the glucosamine release rate does not exceed a rate which results in an adverse change in glucose regulation, e.g., a rate which will induce an insulin resistance response. The rate of release of the glucosamine will preferably be less than about 100 micrograms/min/kg body weight, more preferably less than about 50 micrograms/min/kg body weight, and most preferably less than about 25 micrograms min/kg body weight.

The composition for treatment of arthritis is preferably in a form suitable for oral administration, more preferably in a tablet which contains a high molecular weight HPMC in an amount from about 8 to about 12 wt % as the controlled-release component. The tablet is preferably designed to release the glucosamine at a substantially constant rate over a time period of from about 8 to 12 hours, but not to exceed a rate which results in a glucosamine blood serum level sufficient to affect an adverse change in glucose regulation.

In yet another aspect, the invention is directed towards a method for the treatment of arthritis without adversely effecting glucose regulation, the method involving: administering to a patient having arthritis a composition which contains a therapeutically effective amount of a glucosamine component for the treatment of arthritis dispersed in a controlled-release matrix system capable of releasing the glucosamine in an amount and at a rate sufficient to maintain an effective glucosamine blood serum level for the treatment of arthritis, but not to exceed a glucosamine blood serum level which will affect an adverse change in glucose regulation, over a designated time period.

The composition being administered is preferably the composition for the treatment of arthritis, as described above. This composition is preferably administered orally in a tablet form, more preferably in a tablet which contains HPMC in an amount of from about 8 to about 12 wt %, as the controlled-release component The tablet is preferably designed to release the glucosamine at a substantially constant rate over a time period of about 8 to 12 hours, but not to exceed a rate of about 100 micrograms/min/kg body weight.

In a preferred embodiment, the method will also include maintaining an effective glucosamine blood serum level, by continually repeating the administering step at the expiration of the designated time period, so as to relieve the symptoms of arthritis.

The present invention provides compositions and methods of treatment for conditions having an inflammatory component, which does not have the side effects associated with conventional steroidal anti-inflammatory drugs and NSAIDs, such as aspirin. The present invention also provides the advantage of a composition and method of treatment for arthritis, which does not adversely effect glucose regulation, e.g., does not result in increased insulin resistance in either normal patients or patients with diabetes. Additionally, the present invention is directed to maintaining a substantially constant release rate of glucosamine to provide a better treatment for arthritis as a result of improved patient compliance, a dosage regimen that is easier to use and improved efficiency of the administered glucosamine.

Additional objects, advantages and novel features of the invention will be set forth in part in the description and examples which follow, and in part will become apparent to those skilled in the art upon examination of the following, or may be learned by practice of the invention. The objects and advantages of the invention may be realized and attained by means of the instrumentalities and combinations particularly pointed out in the appended claims.

DETAILED DESCRIPTION OF THE INVENTION

Figure 1:
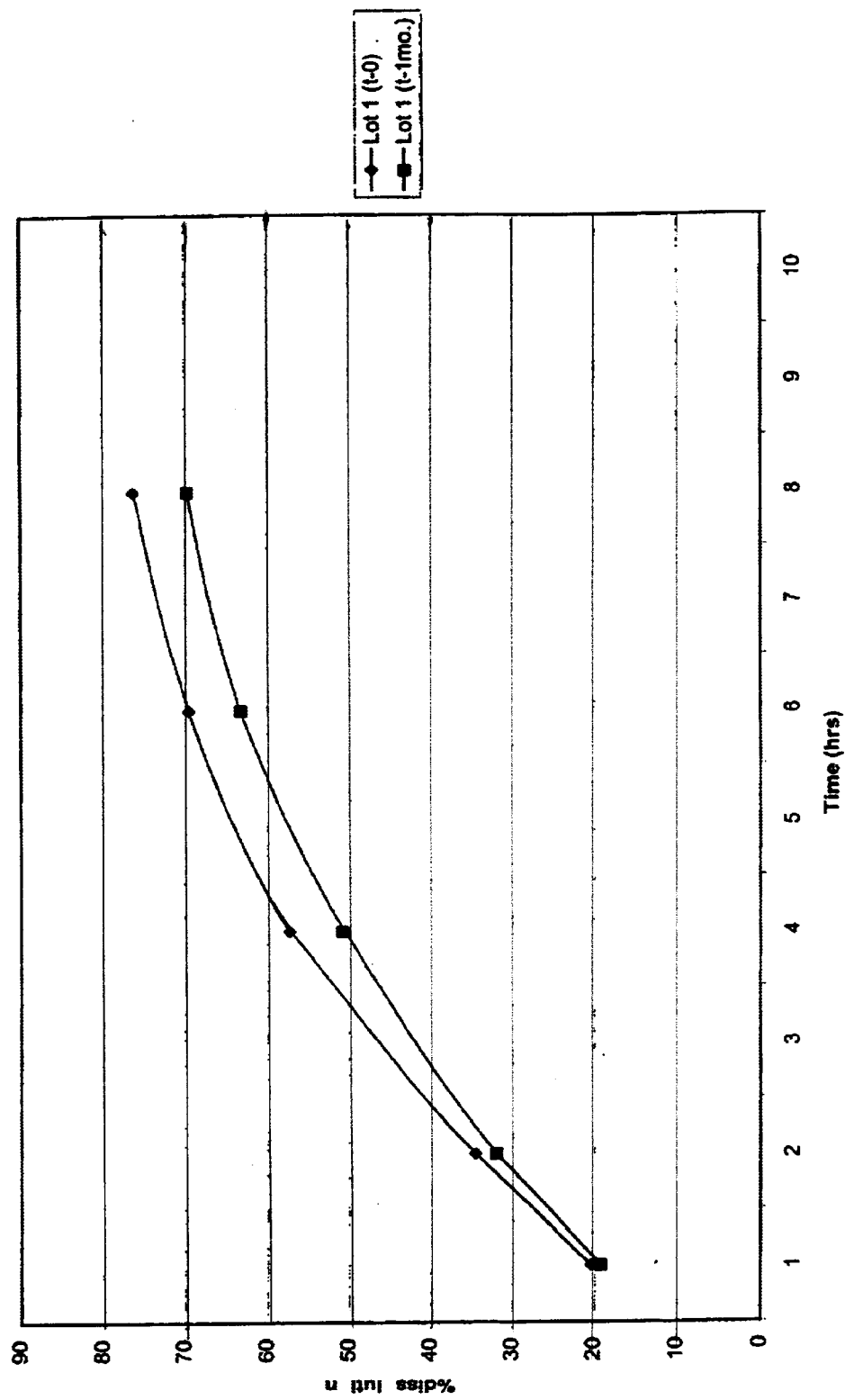
FIG. 1 is a graph of the results of the dissolution tests described in Examples 3 and 4, infra.

The present invention is directed to compositions and methods of treatment for conditions having an inflammatory component, such as, for example, arthritis, including osteoarthritis and rheumatoid arthritis, rheumatism, tendonitis, bursitis, degenerative spinal disc disease, and trauma to joints, tendons, and ligaments.

In one aspect, the invention is directed to a controlled-release glucosamine composition and a method for the treatment of conditions having an inflammatory component, which involves administering glucosamine to a patient having such a condition.

The controlled-release glucosamine composition contains a therapeutically effective amount of a glucosamine component dispersed in a controlled-release matrix system capable of releasing the glucosamine in an amount and at a rate sufficient to maintain an effective glucosamine blood serum level over a designated time period.

The glucosamine component may contain any glucosamine or combination of glucosamines, which exhibit the desired therapeutic effect. Examples of glucosamines which are suitable for the therapeutic composition of the invention include N-acetyl-D-glucosamine (NAG), glucosamine salts, such as glucosamine hydrochloride and glucosamine sulfate, and homologues and analogues of these compounds. The glucosamine component can also be a polymer or copolymer of glucosamine, such as hyaluronic acid, kevatan sulfate, dermatan sulfate, or a polymer or copolymer of galactosamine, such as chondroitin sulfate. The glucosamine component can also be glucosamines and related compounds (or materials) derived from natural sources such as, for example, sea cucumbers, sea cucumber extracts, green lipped mussels and other natural sources of glucosamine. The glucosamine is preferably in a salt form so as to facilitate its delivery and uptake by the human or animal patient. The preferred salt forms are glucosamine sulfate and glucosaminc hydrochloride.

Another element of the composition is the controlled-release matrix system within which the glucosamine is dispersed. The controlled-release matrix system refers to a system containing a matrix, which consists of a continuum of material, and a controlled-release component which is contained by the matrix and which is present in an amount sufficient to provide a highly predictable pre-selected release profile of the therapeutically active glucosamine as a result of normal interaction of the host biosystem on the glucosamine/controlled-release matrix system combination. The controlled release component is preferably finely dispersed throughout the matrix. The glucosamine is preferably finely dispersed throughout the controlled-release matrix system.

The controlled-release component can include one or more ingredients for controlling the rate at which the glucosamine component is made available to the biological system of a host. The controlled-release component can include a sustained release ingredient or a combination of at least two of the following ingredients: an instantaneous release ingredient, a delayed release ingredient or a sustained release ingredient.

An instantaneous release ingredient is self-explanatory in that it refers to an ingredient which promotes or enhances immediate release to the biosystem of the host. The instantaneous release ingredient can be an additional ingredient which enhances dispersion of the glucosamine throughout the bio-system. An example of an instantaneous release ingredient is a surfactant.

A delayed release ingredient is an ingredient which prevents the active ingredient, i.e., glucosamine, from being made available to the host until some time after initial administration. When administration is oral, the delayed release ingredient prevents release of glucosamine until some time in the future. Examples of delayed release ingredients include, but are not limited to, polymeric or biodegradable coatings or matrices, including water soluble cellulose polymers.

A sustained release ingredient is an ingredient, or combination of ingredients, which permits release of the glucosamine to the host at a certain level over a period of time. Examples of sustained release ingredients include gels, waxes, fats, emulsifiers, combinations of fats and emulsifiers, polymers, starch, water soluble cellulose polymers, etc., as well as the above in combination with other polymeric or biodegradable coatings or matrices.

The controlled-release component preferably includes at least one water soluble cellulose polymer. More preferably, the controlled-release component includes at least one water soluble high molecular weight cellulose polymer. High molecular weight cellulose polymer refers to a cellulose polymer having an average molecular weight of at least about 25,000, preferably at least about 65,000, and more preferably at least about 85,000. The exact molecular weight cellulose polymer used will generally depend upon the desired release profile. For example, polymers having an average molecular weight of about 25,000 are useful in a controlled-release composition having a time release period of up to about 8 hours, while polymers having an average molecular weight of about 85,000 are useful in a controlled-release composition having a time released period of up to about 18 hours. Even higher molecular weight cellulose polymers are contemplated for use in compositions having longer release periods. For example, polymers having an average molecular weight of 180,000 or higher are useful in a controlled-release composition having a time release period of 20 hours or longer.

The controlled-release component preferably consists of a water soluble cellulose polymer, preferably a high molecular weight cellulose polymer, selected from the group consisting of hydroxypropyl methyl cellulose (HPMC), hydroxyethyl cellulose (HEC), hydroxypropyl cellulose (HPC), carboxy methyl cellulose (CMC), and mixtures thereof Of these, the most preferred water soluble cellulose polymer is HPMC. Preferably the HPMC is a high molecular weight HPMC, with the specific molecular weight selected to provide the desired release profile.

The water soluble cellulose polymer, e.g., high molecular weight HPMC, is preferably incorporated into the controlled-release matrix system as a fine particulate material having a particle size such that not less than 80% of the particles pass through an 80 mesh screen.

The method of achieving a desired release profile can be varied. For example, the glucosamine can be associated physically (which also includes being chemically associated or bound) with the controlled-release component, within the controlled-release matrix system. Alternatively, the active ingredient, i.e., glucosamine, can be coated, laminated, encapsulated, etc., with the controlled-release component, within the controlled-release matrix system. Regardless of the method of providing the desired release profile, the present invention contemplates use of a controlled-release component containing one or more of the ingredients, as described above.

The glucosamine/controlled-release matrix system combination can be administered in the form of a liquid as a suspension or solution, or alternatively in solid form, such as a tablet, pellet, particle, capsule, or soft gel. For example, the form can be polymeric capsules filled with solid particles which can, in turn, be made to release the glucosamine according to a known pattern or profile. Such particles can also be made to have more than one release profile so that over an extended time the combined release patterns provide a pre-selected profile.

Preferably, the glucosamine/controlled-release matrix system combination is administered in the form of a heterogeneous matrix, such as, for example, a compressed tablet, to control the release of the glucosamine either by diffusion, erosion of the matrix or a combination of both.

Other combinations which are contemplated include a combination of polymeric material(s) and glucosamine which is formed into a sandwich, and which relies on diffusion or erosion to control release of the glucosamine. Additionally, heterogeneous dispersions or solutions of glucosamine in water-swellable hydrogel matrices are useful in controlling the release of the glucosamine by slow surface-to-center swelling of the matrix and subsequent release of the glucosamine by a combination of diffusion of the glucosamine from the water-swollen part of the matrix and erosion of the water-swollen matrix containing the glucosamine.

The controlled-release matrix system will preferably provide for a sustained release of glucosamine according to a desired release profile through the use of one or more of the release ingredients described above. More preferably, the controlled-release matrix system will provide a release profile which releases glucosamine at a substantially constant rate over a designated time period.

As the terminology is used herein, "substantially constant rate" refers to maintaining a release rate of the active ingredient, i.e., glucosamine, within a desired range over at least about 75% of the designated time period for release, preferably over at least about 80% and more preferably over at least about 90% of the designated time period. The desired range for release is preferably about 4.0+/−1.0 percent of the daily dosage of the active ingredient per hour, more preferably about 4.0+/−0.7 percent per hour and most preferably about 4.0+/−0.5 percent per hour. For example, a 12-hour timed-release glucosamine (750 mg of glucosamine) tablet, which releases glucosamine at a substantially constant rate, would maintain a release rate in the range of about 45 to 75 mg per hour over at least 75 percent of the 12 hour period.

A release profile which provides for a substantially constant release rate of glucosamine will result in a more consistent glucosamine blood serum level over the delivery period. As such, the amount of glucosamine delivered can be maximized, while avoiding the side effects attributable to high levels of glucosamine, e.g., inducing an insulin resistance response, and minimizing excessive urinary excretion due to high levels of glucosamine.

It has been found that such a release profile can be obtained through the use of a controlled-release matrix tablet, which contains hydroxypropyl methyl cellulose (HPMC) as the primary ingredient of the controlled-release component. The controlled-release component can also contain minor amounts of other materials which can affect the release profile. Examples of such materials include conventional waxes and waxy materials used in pharmaceutical formulations, such as carnuba wax, spermaceti wax, candellila wax, cocoa butter, cetosteryl alcohol, beeswax, partially hydrogenated vegetable oils, ceresin, paraffin, myristyl alcohol, stearyl alcohol, cetyl alcohol and stearic acid. Hydrophilic gums are also contemplated for use, in minor amounts, which can have an effect on the release profile. Examples of hydrophilic gums include acacia, gelatin, tragacanth, veegum, xanthin gum, carboxymethyl cellulose (CMC), hydroxy propyl cellulose (HPC) and hydroxy ethyl cellulose (HEC).

Preferably, the HPMC in the controlled-release matrix tablet is a high molecular weight HPMC. The specific molecular weight used will typically vary depending upon the desired release profile. For example, a tablet designed to provide a substantially constant release rate over a 12 hour period will preferably contain HPMC having an average molecular weight of at least about 65,000, more preferably about 85,000.

Preferably, the controlled-release matrix tablet will contain about 4 to about 20 wt %, more preferably about 6 to about 16 wt % and most preferably about 8 to about 12 wt % HPMC. The exact amount of HPMC will vary depending upon the molecular weight of the HPMC and the desired release profile. For example, a tablet designed to provide a substantially constant release rate over a 12 hour period, which contains HPMC having a molecular weight of about 85,000, will preferably contain about 8 to about 12 wt %, more preferably about 10%, of the HPMC.

The HPMC used in making the controlled-release tablet will preferably be in the form of a fine particulate having a particle size such that not less than 80% of the HPMC passes through an 80 mesh screen.

The amount of glucosamine contained in the controlled-release tablet will preferably be an amount sufficient to provide a dosage in the range of about 2 mg to about 45 mg of glucosamine per kilogram of body weight per 24 hour period. Preferably, the daily dosage is from about 14 mg to about 29 mg and more preferably about 21 mg per kilogram of body weight. Thus, for a 70 kilogram human or animal, the preferred daily dosage would be in the range from about 250 mg to about 3000 mg, more preferably about 1000 mg to about 2000 mg and most preferably about 1500 mg. Preferably, the controlled-release matrix tablet will provide a release profile which releases the glucosamine at a substantially constant rate over a designated time period. For example, a 12-hour timed-release tablet will release approximately half of the daily dosage at a substantially constant rate over the 12-hour period.

Other ingredients can be used in accordance with the present invention to improve the tablet. The ingredients can be incorporated during the mixing stage, during the agglomeration stage or after the agglomeration stage. Such ingredients include binders, which contribute to the ease of formation and general quality of the tablet; lubricants, which aid in compressing and compacting the tablet; and flow agents or glidants, which adhere to the cohesive material in order to enhance flow properties by reducing interparticle friction.

Examples of useful binders include calcium sulfate, calcium carbonate, microcrystalline cellulose, starches, lactose, sucrose, mannitol, sorbitol, polyvinylpyrrolidone, methylcellulose, sodium carboxymethylcellulose, ethylcellulose, polyacrylamides, polyvinyloxoazolidone, and polyvinylalcohols. A preferred binder is microcrystalline cellulose, such as Avicel PH-101 sold by FMC Corporation.

Lubricants can include, but are not limited to, the following: magnesium stearate, calcium stearate, zinc stearate, stearic acid, hydrogenated vegetable oils, sterotex, polyoxyethylene, monostearate, talc, polyethyleneglycol, sodium benzoate, sodium lauryl sulfate, magnesium lauryl sulfate and light mineral oil. Of these, the preferred lubricants are magnesium stearate and stearic acid.

Flow agents or glidants which can be used include starch, talc, magnesium and calcium stearate, zinc stearate, dibasic calcium phosphate, magnesium carbonate, magnesium oxide, calcium silicate, silicon dioxide and silica aerogels. A preferred flow agent or glidant is silicon dioxide.

In a preferred embodiment, the controlled-release tablet will be made using an ingredient which acts as both a binder and flow agent (or glidant). A suitable source of such an ingredient is Prosolv SMCC 90 sold by Penwest. Prosolv SMCC 90 contains microcrystalline cellulose and lactose bound to a small percentage of silicon dioxide.

A tablet having sufficient mechanical strength and an acceptable release profile can be produced by mixing a powdered glucosamine component with HPMC and suitable binders, lubricants and flow agents and compressing the mixture in a tablet press. A typical compression force used in forming the tablets is in the range of about 45 to about 56 KN, preferably about 50 to about 53 KN, to achieve a tablet having a hardness in the range of about 15 kp to about 30 kp, preferably about 18 kp to about 25 kp.

Glucosamine has been shown to be rapidly and almost completely absorbed into humans and animals after oral administration. The ingested glucosamine is quickly distributed throughout the body and incorporated into glycosaminoglycans and proteoglycans in most tissues and organs. A significant portion of the ingested glucosamine localizes to cartilage and joint tissues, where it remains for long time periods, with excess glucosamine excreted in the urine. This indicates that oral administration of glucosamine reaches connective tissues, where glucosamine is incorporated into newly-synthesized connective tissue.

In vitro, glucosamine has demonstrated increased synthesis of collagen and glycosaminoglycans (or GAG's) from fibroblasts which is the first step in repair of connective tissues. In vivo, topical application of glucosamine has enhanced wound healing. Glucosamine has also exhibited reproducible improvement in symptoms and cartilage integrity in humans and animals with osteoathritis.

Glycosaminoglycans are composed of repeating disaccharide units of glucosamine or glucosamine derivatives, and glucuronic or iduronic acid. Examples of glycosaminoglycans include hyaluronic acid (which is made up of repeating units of glucosamine and glucuronic acid), chondroitin sulphate, dermatan sulphate, keratin sulphate and heparin, all of which contain either glucosamine or the amino sugar galactosamine, which is synthesized from glucosamine. Glycosaminoglycans are also present in proteoglycans, which are structures containing a number of glycosaminoglycan chains linked to a polypeptide or protein core.

Glucosamine plays an important role in the normal maintenance of cell finction, including the permeability of cell membranes, the structural integrity of connective tissues such as skin and cartilage, and joint lubrication. In the intestines and other organs, glycosaminoglycans are essential to the formation of the glycocalyx of gastrointestinal and other organ cells and the mucous secreted by the cells. As well, they are essential components of the extracellular fluid or "glue" which holds cells together, immunoglobulins, blood group antigens and a wide diversity of other biochemically and immunologically important substances.

Although glucosamine is found in all cells and tissues of the body as a component of glycosaminoglycans and proteoglycans, it appears that, unlike glucose, significant concentrations of glucosamine are not available in the blood or intracellular fluids. Under normal conditions, the body utilizes all the available glucosamine it produces. In disease states, such as those involving inflammatory reactions, the body reserves of glucosamine may be inadequate to support cellular repair and function at an optimal level.

The composition of the present invention can also include chondroitin sulfate, as a separate active ingredient. Chondroitin sulfate is a GAG that provides a further substrate for the synthesis of the proteoglycans. The provision of the chondroitin in its salt, sulfate form, facilitates its delivery and update by the host animal. Also, the sulfate is available for further use in catalyzing the conversion of the chondroitin sulfate into proteoglycans.

Chondroitin sulfate not only provides additional organic sulfur to the formula for incorporation into cartilage but it also has a synergistic effect with glucosamine since its structure provides galactosamine which is a different pathway than that used by glucosamine.

The hexosamine and uronic acid pathway is the primary pathway for mucopolysaccharides (GAG) production. Glucosamine is, by far, the more active ingredient.

The daily dosage of the chondroitin sulfate is typically in the range from about 100 mg to about 2400 mg, preferably about 200 mg to about 1800 mg, and more preferably about 1200 mg, for a 70 kilogram human or animal.

The invention is also directed to a unit dosage for controlled delivery of glucosamine.

The unit dosage utilizes the controlled-release glucosamine composition, as described above, to deliver the glucosamine at a substantially constant rate over a designated time period.

Preferably, the unit dosage will have a delivery time period selected from about 6, 8, 12 and 24 hours, which translates to a unit dosage for administration to a patient 4 times per day, 3 times per day, 2 times per day and 1 time per day, respectively, to provide the desired daily dosage.

The unit dosage is preferably a tablet, which contains approximately 8 to 12 wt % HPMC having an average molecular weight of about 85,000 to provide a time release period of about 12 hours.

In another aspect, the invention is a method for the treatment of conditions having an inflammatory component which involves administering to a patient (i.e., human or animal) having a condition with an inflammatory component the controlled-release glucosamine composition. Preferably, the method involves administering the unit dosage, as described above.

In accordance with the method, a unit dosage of the controlled-release glucosamine composition is preferably administered orally in a tablet form. The tablet being administered can have a release time selected from about 6, 8, 12 and 24 hours. Preferably, the tablet will contain HPMC (having a MW of about 85,000) in an amount from about 8 to about 12 wt % and the tablet will release the glucosamine at a substantially constant rate over a period of about 12 hours. In such an embodiment, one unit dosage is normally administered two times a day, i.e., every 12 hours, delivering approximately 1500 mg per day of glucosanine. A relatively constant glucosamine blood serum level can be maintained over an extended period of time by a continued regimen of administering a unit dosage at the expiration of the designated time period, e.g., every 12 hours, so as to relieve the inflammatory component of the condition.

The precise amount of glucosamine per dose may have to be adjusted depending upon the severity of an individual's condition, the extent of progression of the condition, e.g., the extent of damage to connective tissue as a result of arthritis, and the weight of patient being treated. Moreover, once the progression of the condition has been arrested, the regimen can be continued to maintain the individuals relief from the symptoms of the inflammatory condition, but a change in the amount of glucosamine may be warranted.

In another aspect, the invention is directed towards a composition for the treatment of arthritis, which does not adversely effect glucose regulation. The composition contains a combination of a therapeutically effective amount of a glucosamine component dispersed in a controlled-release matrix system capable of releasing the glucosamine in an amount and at a rate sufficient to maintain an effective glucosamine blood serum level for treatment of arthritis, but not to exceed a glucosamine blood serum level which will affect an adverse change in glucose regulation, over a designated time period.

The adverse change in glucose regulation refers to increased difficulty in metabolizing blood serum glucose and is generally manifested in increased insulin resistance, which is induced by high glucosamine levels. Thus, by controlling the maximum rate of release, an insulin resistance response can be avoided.

The glucosamine release rate is controlled so that it is less than 100 micrograms/min/kg body weight. Preferably, the release rate is less than about 50 and more preferably less than about 25 micrograms/min/kg body weight.

This composition for treating arthritis is preferably similar to the controlled-release glucosamine composition and unit dosage, discussed above, with the proviso that the glucosamine blood serum level must not exceed a level which results in an adverse change in glucose regulation, e.g., induces an insulin resistance response, in a normal individual (i.e., individual which does not have diabetes), a patient suffering from either diabetes mellitus or syndrome X, or an individual predisposed to such conditions.

Preferably, the composition is in a form suitable for oral administration and the controlled-release matrix system releases the glucosamine at a rate sufficient to maintain an essentially constant glucosamine blood serum level over a designated time period, but not exceeding a release rate of 100 microgram/minlkg body weight.

In yet another aspect, the invention is directed towards a method for the treatment of arthritis which does not effect an adverse change in glucose regulation. The method involves a regiment of administering a unit dosage of glucosamine via the controlled-release composition in an amount and at a rate which is sufficient to treat the arthritic condition, but not resulting in a glucosamine blood serum level which affects an adverse change in glucose regulation, e.g., a level which induces an insulin resistance response.

Preferably, the regimen will include administering a unit dosage every 12 hours, in which the unit dosage delivers glucosamine at a rate below about 100 micrograms/min/kg body weight until the symptoms of the arthritic condition are relieved.

EXAMPLES

The following non-limiting examples have been carried out to illustrate preferred embodiments of the invention. These examples include the preparation of unit dosage tablets according to the invention and evaluation of the release profiles of the controlled-release tablets.

Example 1

Controlled-release glucosamine sulfate tablets are formed as follows: 2,469 grams of glucosamine sulfate (in powder form) is combined with 549 grams of Prosolv SMCC 90, 337 grams of HPMC (MW=85,000, Particle size=NLT 80% through an 80 mesh screen), 75 grams of stearic acid NF and 19 grams of magnesium stearate NF. The combination is placed in a V-blender and mixed for 10 minutes. The mixture is compressed on a 16 station rotary press to produce about 3000 tablets, each containing about 700 milligrams of glucosamine sulfate. Each tablet will weigh approximately 1150 milligrams.

Example 2

Controlled-release glucosamine hydrochloride tablets, also containing chondroitin sulfate are formed as follows: 1,763 grams of glucosamine HCl (in powder form) is combined with 713 grams of chondroitin sulfate, 529 grams of Prosolv SMCC 90, 356 grams of HPMC, 198 grams of stearic acid NF and 19 grams of Magnesium stearate. The combination is placed in a v-blender and mixed for 10 minutes. The resulting mixture is compressed on a 16 station rotary press, to produce about 3000 tablets, each containing approximately 500 milligrams of Glucosamine HCl and 200 milligrams of Chondroitin sulfate. Each tablet will weigh approximately 1190 milligrams.

Example 3

A dissolution test on a timed-release glucosamine tablet was conducted using a standard paddle dissolution apparatus as follows: a dissolution vessel having a volume of 200 milliliters was filled with D.I. water and a 1350 mg tablet ("Lot 1") containing approximately 750 mg of glucosamine sulfate and approximately 11 wt % HPMC (MW=85,000 Particle size=NLT 80% through an 80-mesh screen) was dropped into the water with the paddle turning. The water temperature was maintained at about 37° C. Aliquots of the solution in the dissolution vessel were taken at hours 1, 2, 4, 6 and 8 and analyzed using standard HPLC techniques to measure the concentration of glucos amine sulfate. The results are plotted in FIG. 1.

Example 4

Example 3 was repeated using a similar tablet that was aged approximately one month at about 40° C. and 70% RH. The results are also plotted in FIG. 1.

A review of FIG. 1 reveals that the glucosamine sulfate was released from each of the tablets (i.e., fresh tablet and 1 month aged tablet) at a relatively constant rate over the majority of the 8-hour test period.

Example 5

A dissolution test on a timed-release glucosamine sulfate –2KCl tablet was conducted using a standard dissolution apparatus as follows: a dissolution vessel having a volume of 200 milliliters was filled with D.I. water and a sample tablet was dropped into the water with the paddle turning at 75 rpm. The water temperature was set at 37° C. Aliquots of the solution in the dissolution vessel were taken at hours 1, 2, 4, 6 and 8 and analyzed by HPLC to measure the concentration of glucosamine sulfate –2KCl. The test was repeated for 6 sample tablets taken from the same sample lot and the results represent an average of the 6 dissolution tests. The average tablet weight of the sample lot was 1258.6 mgs. with each tablet containing an estimated 801.2 mgs. of glucosamine sulfate –2KCl and approximately 9 wt % HPMC (MW=85,000, Particle size NCT 80% through an 80 mesh screen). The results are plotted in FIG. 2.

Example 6

Example 5 was repeated using tablets from a sample lot having an average tablet weight of 1287.7 mgs. with each tablet containing an estimated 791.8 mgs. of glucosamine sulfate .2KCl and approximately 11 wt % HPMC (MW=85,000 Particle size=MLT 80% through an 80 mesh screen). The results are plotted in FIG. 2.

Figure 2:
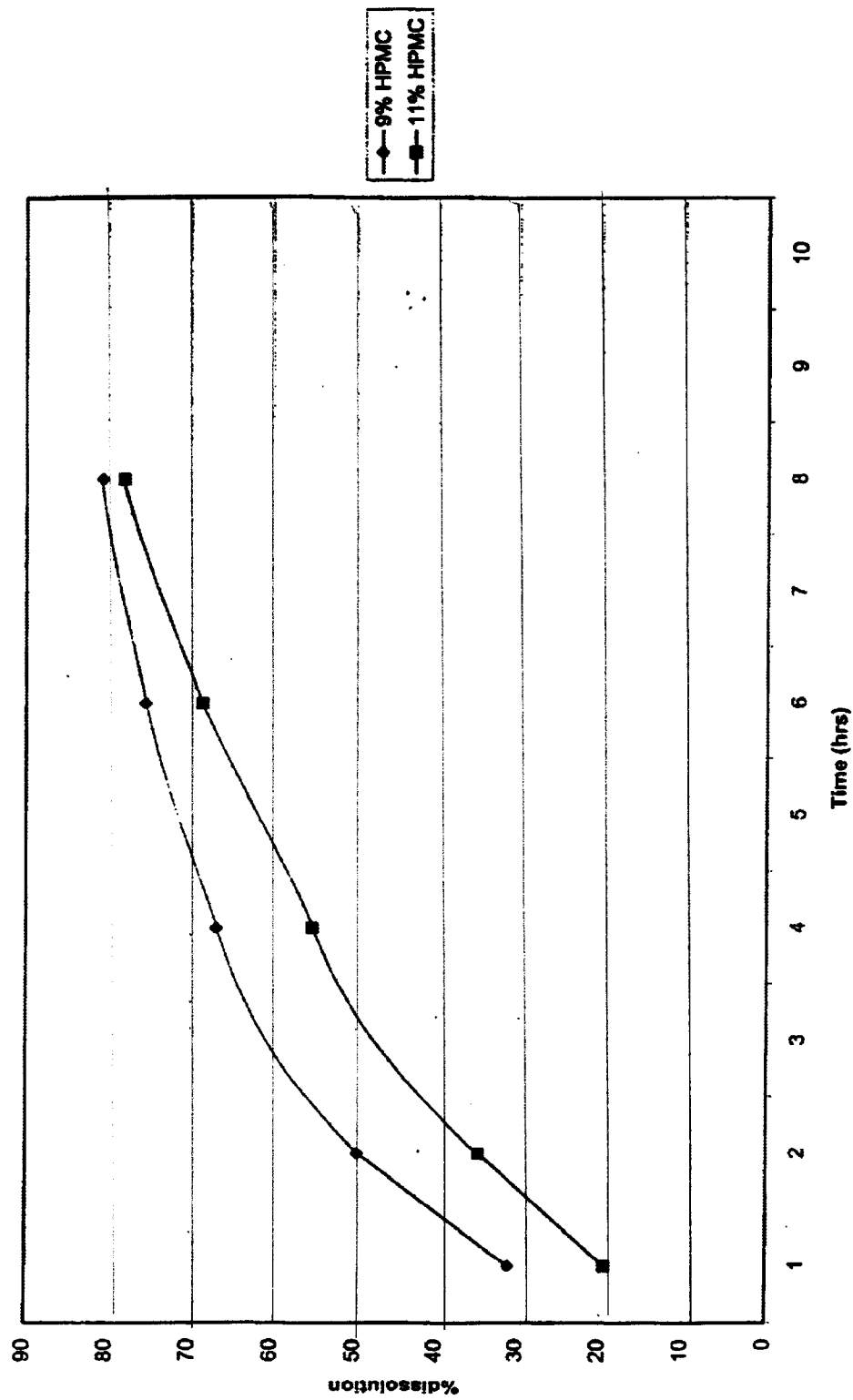
FIG. 2 is a graph of the results of the dissolution tests described in Examples 5 and 6, infra.

A review of FIG. 2 reveals that the overall rate of dissolution of the glucosamine sulfate decreases with an increasing percentage of HPMC in the tablet.

Example 7

Figure 3:
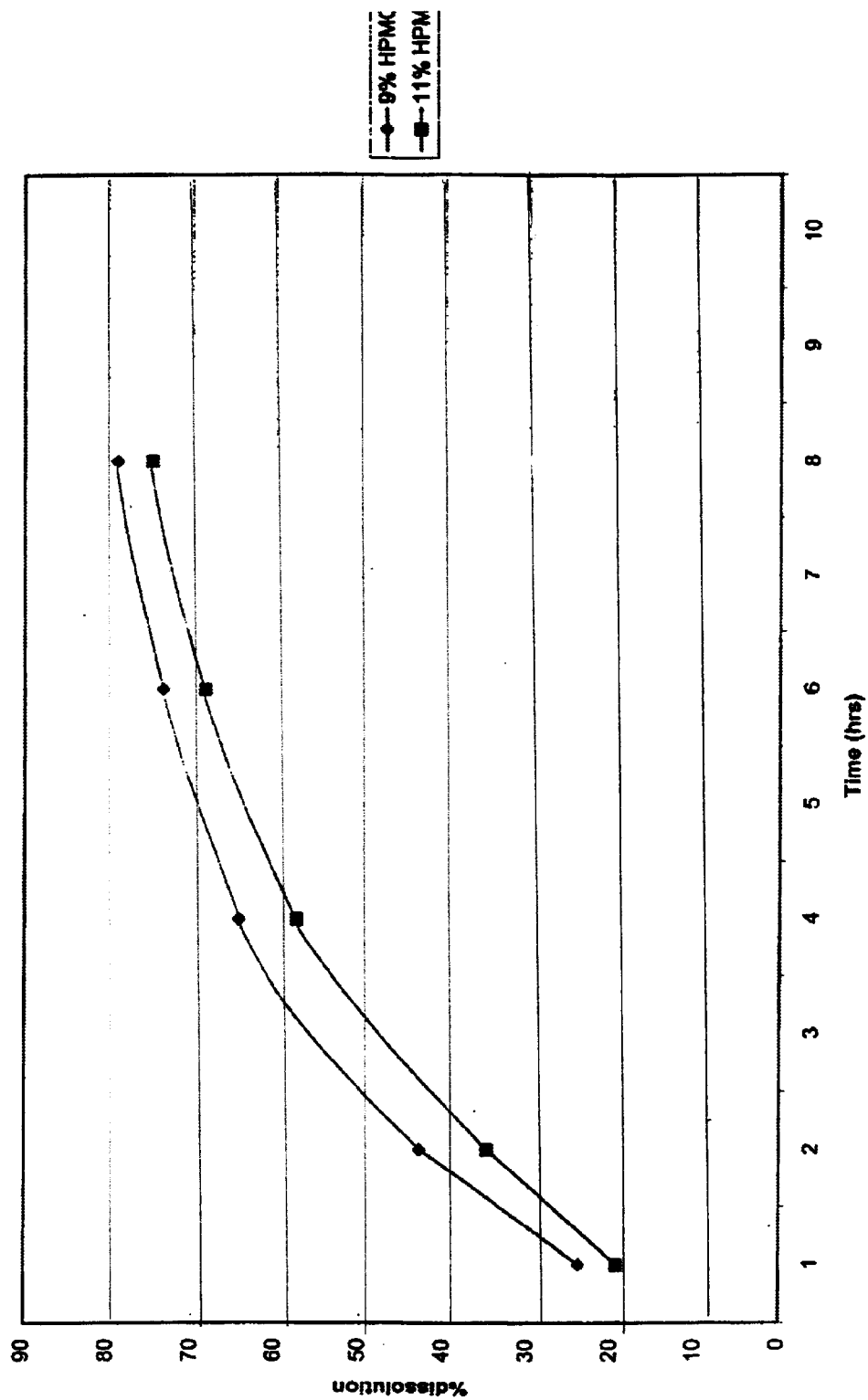
FIG. 3 is a graph of the results of the dissolution tests described in Example 7, infra.

Examples 5 and 6 were repeated using tablets from the same sample lots, respectfully, but which were aged approximately 1 month at about 40° C. and 70% RH. The results are plotted in FIG. 3.

A review of FIG. 3, again reveals that the overall rate of dissolution of the glucosamine sulfate from the one month aged tablets decreases with an increasing amount of HPMC in the tablet.

Example 8

Example 7 was repeated using tablets that were aged approximately 2 months at about 40° C. and 70% RM. The results are plotted in FIG. 4.

Figure 4:
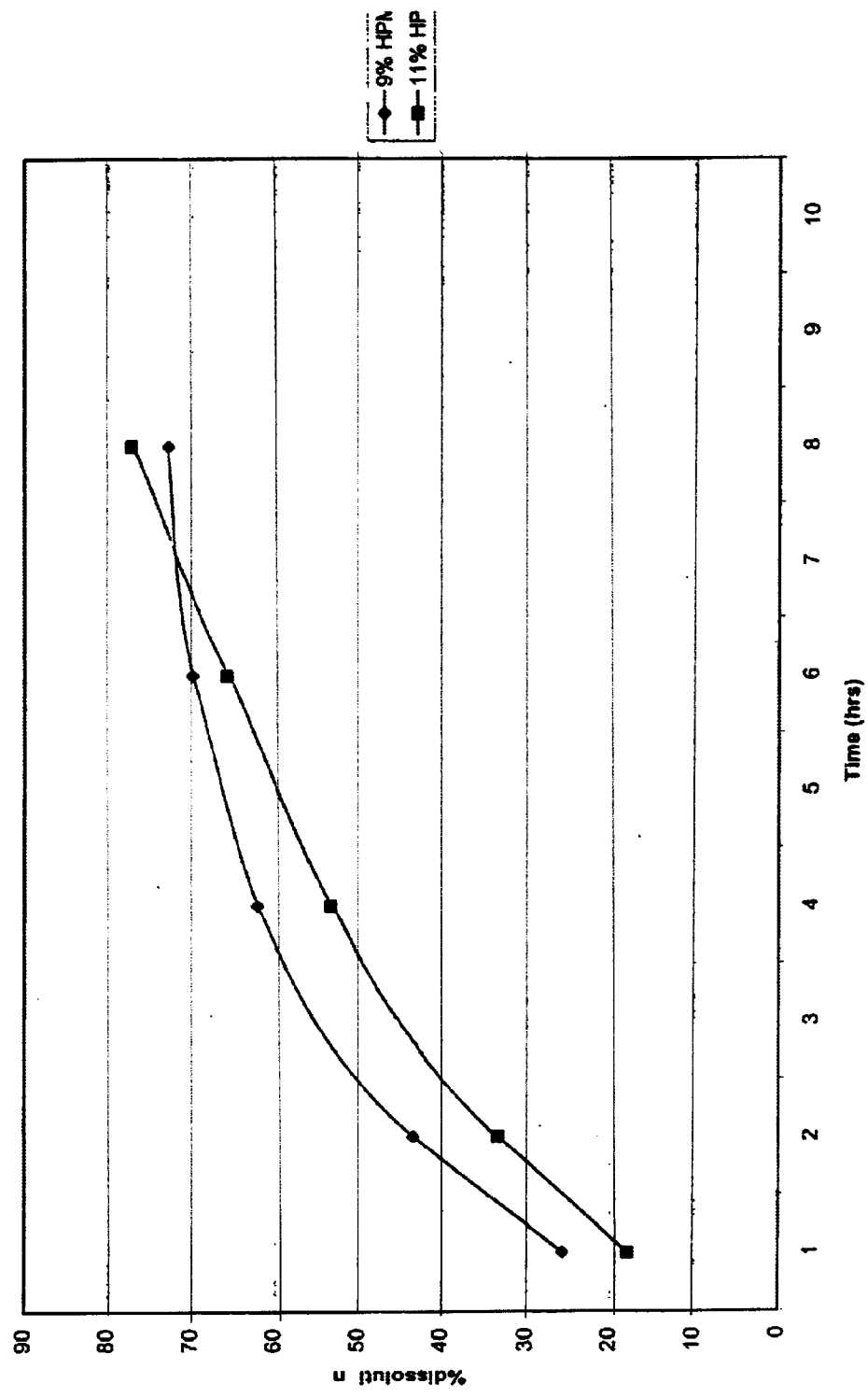
FIG. 4 is a graph of the results of the dissolution tests described in Example 8, infra

A review of FIG. 4, reveals that the results are generally consistent with Examples 5, 6 and 7. The data points at 8 hours on FIG. 4, which show that a greater percentage of glucosamine sulfate dissolved out of the tablet containing a higher amount of HPMC, may be a result of experimental error, contamination or deviation in the sample lot used.

Example 9

Example 7 was repeated using tablets that were aged approximately 3 months at about 40° C. and 70% RH. The results are plotted in FIG. 5.

Figure 5:
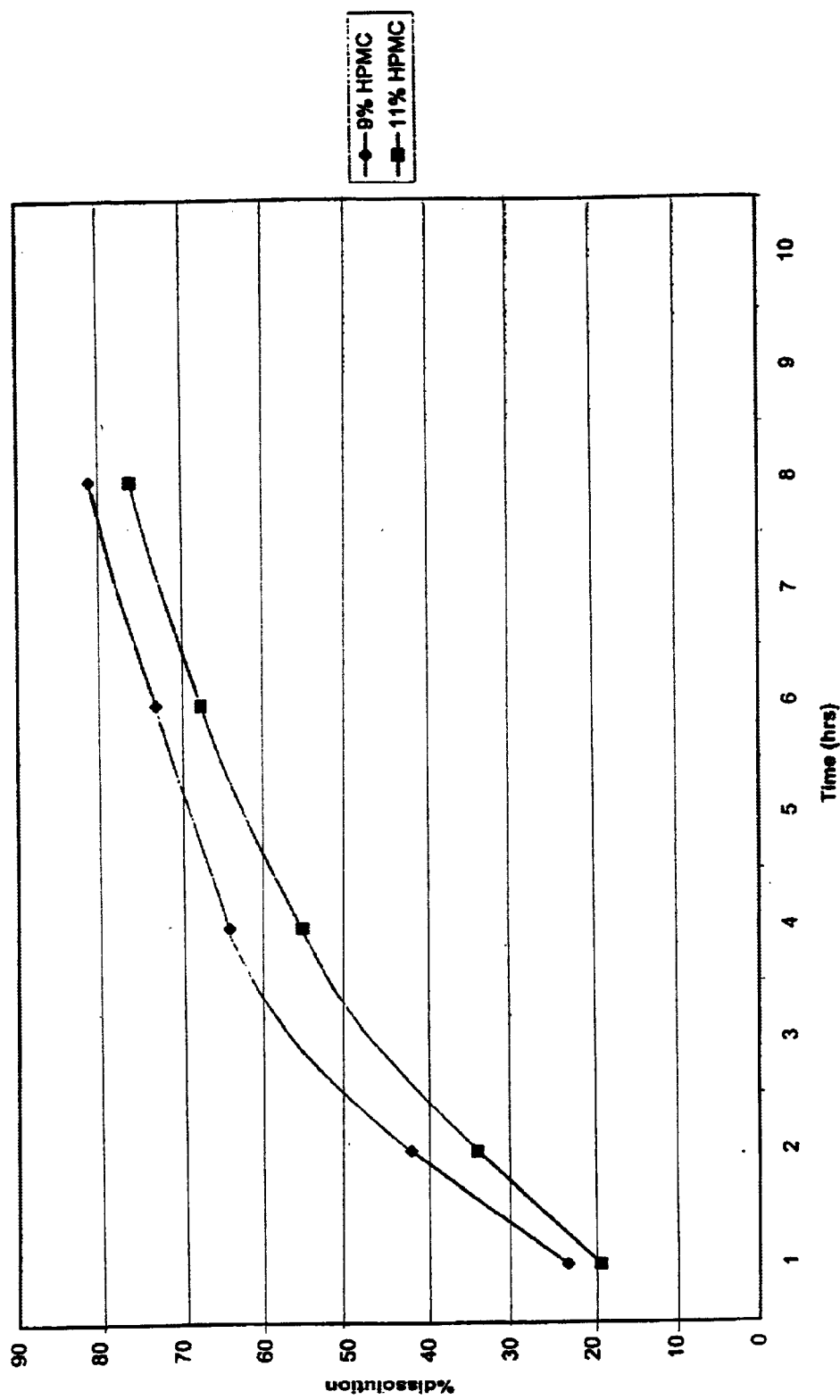
FIG. 5 is a graph of the results of the dissolution tests described in Example 9, infra

A review of FIG. 5, reveals that results of the 3 month aged tablets are consistent with Examples 5, 6 and 7.

Thus, while there has been disclosed what is presently believed to be the preferred embodiments of the invention, those skilled in the art will appreciate that other and further changes and modifications can be made without departing from the scope or spirit of the invention, and it is intended that all such other changes and modifications are included in an are within the scope of the invention as described in the appended claims.

We claim:

1. A controlled-release glucosamine composition comprising a therapeutically effective amount of a glucosamine component dispersed in a controlled-release matrix system, said matrix system comprising a continuum of material and a controlled-release component finely dispersed throughout said matrix system and capable of releasing said glucosamine in an amount and at a rate sufficient to maintain an effective glucosamine blood serum level over a designated time period, said controlled-release component comprising at least one water soluble high molecular weight cellulose polymer.

2. A controlled-release glucosamine composition of claim 1, wherein said glucosamine component is selected from the group consisting of N-acetyl-D-glucosamine, glucosamine hydrochloride, glucosamine sulfate and mixtures thereof.

3. A controlled-release glucosamine composition of claim 2, wherein a daily dosage of said glucosamine ranges from about 2 mg to about 45 mg per kilogram of body weight.

4. A controlled-release glucosamine composition of claim 3, wherein said daily dosage is from about 14 mg to about 29 mg per kilogram of body weight.

5. A controlled-release glucosamine composition of claim 4, wherein said daily dosage is about 21 mg per kilogram of body weight.

6. A controlled-release glucosamine composition of claim 1, wherein said controlled-release component is selected from the group consisting of hydroxypropyl methyl cellulose (HPMC), hydroxy ethyl cellulose (HEC), hydroxy propyl cellulose (HPC), carboxy methyl cellulose (CMC), and mixtures thereof.

7. A controlled-release glucosamine composition of claim 6, wherein said controlled-release component is a high molecular weight HPMC.

8. A controlled-release glucosamine composition of claim 7, wherein said HPMC consists of fine particulates having a particle size such that not less than 80% of the HPMC particles pass through an 80 mesh screen and said HPMC is present in an amount from about 8 to about 12 wt %, based upon total weight of the composition.

9. A controlled-release glucosamine composition of claim 1, wherein said composition is in a form suitable for oral administration.

10. A controlled-release glucosamine composition of claim 1, wherein said controlled-release matrix system is capable of releasing said glucosamine at a substantially constant rate over a designated time.

11. A controlled-release glucosamine composition of claim 10, wherein said designated time period is selected from the group consisting of about 6, 8, 12 and 24 hours.

12. A controlled-release glucosamine composition of claim 11, wherein said designated time period is about 12 hours.

13. A controlled-release glucosamine composition of claim 1, further comprising a therapeutically effective amount of chondroitin sulfate.

14. A unit dosage for controlled delivery of glucosamine comprising a glucosamine component dispersed in a controlled-release matrix system, and matrix system comprising a continuum of material and a controlled-release component finely dispersed throughout said matrix system and capable of providing a release profile which results in a substantially constant glucosamine release rate over a designated time period.

15. The unit dosage of claim 14, which is a tablet.

16. The unit dosage of claim 15, wherein said controlled-release component is HPMC present in an amount of from about 8 to about 12 wt %, said HPMC having a molecular weight of about 85,000, and wherein said designated time period is about 12 hours.

17. A method for the treatment of conditions having an inflammatory component comprising:
administering to a human or animal having a condition with an inflammatory component a composition which contains a therapeutically effective amount of a glucosamine component dispersed in a controlled-release matrix system, said matrix system comprising a continuum of material and a controlled-release component finely dispersed throughout said matrix system and capable of releasing said glucosamine in an amount an at a rate sufficient to maintain an effective glucosamine blood serum level over a designated time period, said controlled-release component comprising at least one water soluble high molecular weight cellulose polymer.

18. A method of claim 17, wherein said glucosamine component is selected from the group consisting of N-acetyl-D-glucosamine, glucosamine hydrochloride, glucosamine sulfate and mixtures thereof.

19. A method of claim 17, wherein a daily dosage of said glucosamine ranges from about 14 mg to about 29 mg per kilogram of body weight.

20. A method of claim 17, wherein said composition is in a tablet form.

21. A method of claim 20, wherein said tablet comprises a high molecular weight HPMC in an amount from about 8 to about 12 wt %.

22. A method of claim 21, wherein said tablet releases said glucosamine at a substantially constant rate over a designated time period.

23. A method of claim 22, further comprising:
maintaining a substantially constant glucosamine release rate, by continually repeating the administering step at the expiration of said designated time period, so as to relieve the inflammatory component of said condition.

24. A method of claim 22, wherein said designated time period is approximately 12 hours.

25. A composition for the treatment of arthritis without adversely effecting glucose regulation, said composition comprising a therapeutically effective amount of a glucosamine component dispersed in a controlled-release matrix system, said matrix system comprising a continuum of material and a controlled-release component finely dispersed throughout said matrix system and capable of releasing said glucosamine in an amount and at a rate sufficient to maintain an effective glucosamine blood serum level for treatment of arthritis, but not to exceed a glucosamine blood serum level which will affect an adverse change in glucose regulation, over a designated time period.

26. A composition of claim 25, wherein said adverse change in glucose regulation is manifested by increased insulin resistance.

27. A composition of claim 25, wherein said glucosamine component is selected from the group consisting of N-acetyl-D-glucosamine, glucosamine hydrochloride, glucosamine sulfate and mixtures thereof.

28. A composition of claim 25, wherein a daily dosage of said glucosamine ranges from about 14 mg to about 29 mg per kilogram of body weight.

29. A composition of claim 25, wherein said rate is less than 100 micrograms/min/kg body weight.

30. A composition of claim 25, wherein said composition is in a form suitable for oral administration.

31. A composition of claim 25, wherein said controlled-release matrix system releases said glucosamine at a substantially constant rate over a designated time period.

32. A composition of claim 31, wherein said composition is in the form of a tablet.

33. A composition of claim 32, wherein said tablet comprises a high molecular weight HPMC in an amount from about 8 to about 12 wt %.

34. A composition of claim 33, wherein said designated time period is approximately 12 hours.

35. A method for the treatment of arthritis without adversely effecting glucose regulation, said method comprising:

administering to a patient having arthritis a composition which comprises a therapeutically effective amount of a glucosamine component for the treatment of arthritis dispersed in a controlled-release matrix system, said matrix system comprising a continuum of material and a controlled-release component finely dispersed throughout said matrix system and capable of releasing said glucosamine in an amount and at a rate sufficient to maintain an effective glucosamine blood serum level for the treatment of arthritis, but not to exceed a glucosamine blood serum level which will affect an adverse change in glucose regulation, over a designated time period.

36. A method for the treatment of arthritis of claim 35, wherein said patient has both arthritis and diabetes.

37. A method for the treatment of arthritis of claim 35, wherein said adverse change in glucose regulation is manifested by increased insulin resistance.

38. A method for the treatment of arthritis of claim 35, wherein said glucosamine component is selected from the group consisting of N-acetyl-D-glucosamine, glucosamine hydrochloride, glucosamine sulfate and mixtures thereof.

39. A method for the treatment of arthritis of claim 35, wherein a daily dosage of said glucosamine ranges from about 14 mg to about 29 mg per kilogram of body weight.

40. A method for the treatment of arthritis of claim 35, wherein said composition is in a tablet form.

41. A method for the treatment of arthritis of claim 40, wherein said tablet releases said glucosamine at a substantially constant rate over a designated time period.

42. A method for the treatment of arthritis of claim 41, wherein said tablet comprises a high molecular weight HPMC in an amount from about 8 to about 12 wt %.

43. A method for the treatment of arthritis of claim 42, wherein said designated time period is approximately 12 hours.

44. A method for the treatment of arthritis of claim 35, wherein said rate is less than 100 micrograms/min/kg body weight.

45. A method for the treatment of arthritis of claim 35, further comprising:

maintaining said glucosamine blood serum level, by continually repeating the administering step at the expiration of said designated time period, so as to relieve the symptoms of arthritis.

46. A method for the treatment of arthritis of claim 45, wherein said designated time period is approximately 12 hours.

* * * * *

UNITED STATES PATENT AND TRADEMARK OFFICE
CERTIFICATE OF CORRECTION

PATENT NO. : 6,767,899 B1
DATED : July 27, 2004
INVENTOR(S) : Kay et al.

It is certified that error appears in the above-identified patent and that said Letters Patent is hereby corrected as shown below:

Column 2,
Line 12, now reads "ofjoint (rheumatoid arthritis,", and should read -- of joint (rheumatoid arthritis, --;
Line 66, now reads "54Edition, 2000", and should read -- 54th Edition, 2000 --;

Column 4,
Line 5, now reads "rebuilding ofjoint tissues.", and should read -- rebuilding of joint tissues. --;
Line 11, now reads "rebuilding ofjoint tissues,", and should read -- rebuilding of joint tissues, --;

Column 5,
Line 21, now reads "thereof A typical dosage", and should read -- thereof. A typical dosage --;

Column 9,
Line 56, now reads "mixtures thereof Of these", and should read -- mixtures thereof. Of these --;

Column 14,
Line 6, now reads "per day glucosanine.", and should read -- per day of glucosamine. --;
Line 56, now reads "100 microgram/min body weight", and should read
-- 100 microgram/min/kg body weight --;

Column 16,
Line 56, now reads "aged tablcts are consistent", and should read -- aged tablets are consistent --;

Signed and Sealed this

Eighth Day of February, 2005

JON W. DUDAS
*Director of the United States Patent and Trademark Office*